United States Patent
Nakada et al.

(10) Patent No.: US 6,328,907 B1
(45) Date of Patent: *Dec. 11, 2001

(54) AZEOTROPE COMPRISING PENTAFLUOROPROPANE AND HYDROGEN FLUORIDE AND METHOD FOR SEPARATING AND PURIFYING PENTAFLUOROPROPANE

(75) Inventors: Tatsuo Nakada; Noriaki Shibata; Takashi Shibanuma, all of Osaka (JP)

(73) Assignee: Daikin Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,809

(22) PCT Filed: Jan. 22, 1997

(86) PCT No.: PCT/JP97/00134

§ 371 Date: Jul. 23, 1998

§ 102(e) Date: Jul. 23, 1998

(87) PCT Pub. No.: WO97/27163

PCT Pub. Date: Jul. 31, 1997

(30) Foreign Application Priority Data

Jan. 23, 1996 (JP) .................................. 8-009085
Jun. 18, 1996 (JP) .................................. 8-156701

(51) Int. Cl.[7] .............................. C09K 5/04; C07C 17/38
(52) U.S. Cl. .......................... 252/67; 510/408; 510/412; 570/177; 570/178; 570/180
(58) Field of Search .................... 510/408, 412; 252/67; 570/177, 178, 180

(56) References Cited

U.S. PATENT DOCUMENTS

| | | | |
|---|---|---|---|
| 5,461,177 | * 10/1995 | Manzer et al. | 570/178 |
| 5,574,192 | * 11/1996 | VanDerPuy et al. | 570/167 |
| 5,616,819 | * 4/1997 | Boyce et al. | 570/167 |
| 5,874,658 | * 2/1999 | Belter | 570/180 |
| 5,895,639 | * 4/1999 | Swain et al. | 423/483 |
| 6,001,796 | * 12/1999 | Pham et al. | 510/408 |
| 6,060,629 | * 5/2000 | Pham et al. . | |

FOREIGN PATENT DOCUMENTS

| | | |
|---|---|---|
| 4261126 | 9/1992 | (JP) . |
| 5178768 | 7/1993 | (JP) . |
| 97/05089 | * 2/1997 | (WO) . |
| WO9705089 | 2/1997 | (WO) . |
| 98/00381 | * 1/1998 | (WO) . |
| WO9800381 | 1/1998 | (WO) . |

OTHER PUBLICATIONS

English language abstract of EP-A-703205, Mar. 1996.
English language abstract of EP-A-676386, Oct. 1995.
English language abstract of EP-A-542290, May 1993.

* cited by examiner

*Primary Examiner*—Margaret Einsmann
(74) *Attorney, Agent, or Firm*—Birch, Stewart, Kolasch & Birch, LLP

(57) ABSTRACT

There is provided an azeotropic mixture consisting substantially of 1,1,1, 3,3-pentafluoropropane and hydrogen fluoride. Further, there is provided a process of separating/purifying R-245fa and/or HF from a mixture comprising R-245fa and HF wherein the mixture comprising 1,1,1,3,3-pentafluoropropane and hydrogen fluoride is subjected to a distillation step so that a distillate is obtained which comprises the azeotropic mixture consisting substantially of 1,1,1,3,3-pentafluoropropane and hydrogen fluoride, and a bottom product is obtained which comprises separated/purified 1,1,1,3,3-pentafluoropropane or hydrogen fluoride.

4 Claims, 5 Drawing Sheets

AZEOTROPE COMPRISING PENTAFLUOROPROPANE AND HYDROGEN FLUORIDE AND METHOD FOR SEPARATING AND PURIFYING PENTAFLUOROPROPANE

This application claims the benefit under 35 U.S.C. §371 of prior PCT International Application No. PCT/JP97/00134 which has an international filing date of Jan. 22, 1997 which designated the united states of America, the entire contents of which are hereby incorporated by references.

TECHNICAL FIELD

The present invention relates to an azeotropic mixture of 1,1,1,3,3-pentafluoropropane (which hereinafter may be referred to as also "R-245fa") and hydrogen fluoride (which hereinafter may be referred to as also "HF"), and a process of separating/purifying R-245fa and/or hydrogen fluoride from a mixture comprising at least R-245fa and hydrogen fluoride.

BACKGROUND ART

R-245fa is a useful compound which can be used for an alternative for CFC (chlorofluorocarbon) or HCFC (hydrochlorofluorocarbon) used as a cooling medium and a foaming agent and which is not likely to destroy the ozone layer.

R-245fa can be produced by fluorination of 1,1,1,3,3-pentachloropropane using HF. In this production process, since an excessive amount of HF is used for the reaction, a reaction mixture contains a considerable amount of unreacted HF in addition to produced R-245fa, and also may contain, in addition to these, a by-product (for example, R-244fa (1,1,1,3-tetrafluoro-3-chloropropane) and so on). A composition of such a reaction mixture is determined by reaction conditions, and in order to obtain R-245fa from the reaction mixture as described above, the mixture is subjected to separation/purification. Further, it is desirable to recover the unreacted HF from the reaction mixture and re-used for the reaction.

In the present specification, the term "separate/purify" is intended to mean such that when a mixture stream comprising specific two components (for example, R-245fa and HF) is subjected to a certain processing step (for example, a distillation step) and thereby other stream is obtained in which stream a ratio of a concentration (a) of one specific component (for example, R-245fa) to a concentration (b) of the other specific component (for example, HF) of the stream (namely a ratio [a/b]) is increased, that is when the ratio [a/b] is increased to [a'/b'] (wherein a'/b'>a/b), the specific component (R-245fa) is said to be separated/purified.

Further, in the present specification, the term "separate/purify" is intended to not necessarily mean perfect separation, and such term is used to include a fairly broad meaning so that it includes a concept of so-called "concentration." However, in one of the most preferable embodiments, the term "separate/purify" is intended to mean that a mixture stream consisting substantially of two specific components is subjected to a predetermined step so that other stream is obtained which contains substantially only one specific component. In another embodiment of the most preferable embodiments, the term "separate/purify" is intended to mean that a mixture stream consisting substantially of two specific components and at least one component is subjected to a predetermined step so that other stream is obtained which is substantially free from one of the specific components.

When R-245fa is separated/purified from a reaction mixture as described above, alkaline washing and/or water washing is usually used for the separation of unreacted HF from R-245fa (and other HFC if any). However, separated HF in such a manner is present in an aqueous solution and there is no other way than disposing it. Thus, the above mentioned separation not only wastes HF but also requires additional cost for washing and disposing. Therefore, it is desirable to provide a process of more effectively separating/purifying R-245fa and/or HF from a mixture of HF and R-245fa.

As to other HFCs such a s R-134a (1,1,1,2-tetrafluoroethane), there are examples in which using an azeotropic mixture of HF and the HFC, separating R-134a is separated from a mixture containing those compounds (see, for example, Japanese Patent Kokai Publication Nos. 4-261126 and 5-178768). However, with respect to the separation of R-245fa and/or HF from a mixture of R-245fa and HF, the presence of an azeotropic mixture of R-245fa and HF has not been known.

DISCLOSURE OF THE INVENTION

It is an object of the present invention to provide a process of separating/purifying R-245fa and/or HF from a mixture comprising at least R-245fa and HF without a washing step as described above.

The present inventors have intensively studied the process of separating/purifying R-245fa and/or HF from the mixture comprising at least R-245fa and HF, and have found for the first time that R-245fa and HF form a minimum azeotropic mixture and completed the present inventions.

Thus, the present invention provides an azeotropic mixture consisting substantially of 1,1,1,3,3-pentafluoropropane and hydrogen fluoride. The azeotropic mixture is a minimum azeotropic mixture having a minimum boiling point. An azeotropic temperature and an azeotropic composition of the azeotropic mixture depend on a pressure of a system in which the azeotropic mixture is formed. Typical azeotropic temperatures and compositions are shown below which were measured in Example 2 which will be described below:

| Pressure ($kg/cm^2$-gauge) | Azeotropic Temperature (° C.) | Azeotropic Composition (mol % of R-245fa) |
|---|---|---|
| 2.95 | 40 | 34.5 |
| 3.50 | 45 | 40.8 |
| 4.20 | 50 | 45.0 |
| 5.80 | 60 | 48.2 |
| 7.00 | 67 | 48.5 |
| 7.65 | 70 | 47.4 |
| 9.00 | 77 | 42.1 |
| 9.60 | 80 | 36.3 |

The above azeotropic mixture has been found for the first time by the present inventors.

The azeotropic mixture can be used as reflux of a distillation step in which R-245fa or HF is separated/purified from a mixture comprising R-245fa and HF. In the distillation step, the mixture containing R-245fa and HF at any ratio of R245fa/HF is supplied to the distilling step as a feed, and R-245fa and HF are distilled off from the distilling step as an azeotropic mixture and a bottom product is obtained which has a higher or lower R-245fa/HF ratio, then that of the feed depending on the R245fa/HF ratio of the feed, whereby effective separation/purification of R-245fa or HF is possible.

That is, the present invention provides a process of separating/purifying 1,1,1,3,3-pentafluoropropane or hydrogen fluoride in which a mixture comprising at least 1,1,1,3,3-pentafluoropropane and hydrogen fluoride as a feed is subjected to a distillation step so that a distillate is obtained which comprises an azeotropic mixture consisting substantially of 1,1,1,3,3-pentafluoropropane and hydrogen fluoride and a bottom product is obtained which comprises separated/purified 1,1,1,3,3-pentafluoropropane or hydrogen fluoride.

The feed which can be used in the present process comprises at least R-245fa and HF, and in a preferred embodiment, the feed consists substantially of R-245fa and HF. In the latter embodiment, the azeotropic mixture is substantially distilled off and R-245fa which contains substantially no HF or HF which contains substantially no R-245fa is obtained as a bottom product. Optionally, the feed may contain other component such as 1,1,1,3,3-pentachloropropane, 1,1,1,3-tetraluoro-3-chloropropane and so on. Such other component(s) is merely distributed to the distillate or the bottom product depending on its boiling point at an operation pressure of the distillation step and an azeotropic temperature of the other component and HF if they form another azeotropic mixture. As a concrete example, the feed may be a reaction mixture obtained upon the production of R-245fa from pentachloropropane and HF.

When a ratio of R-245fa/HF of the feed is smaller than that of an azeotropic mixture which is formed at an operation pressure of the distillation step, a distillation bottom product comprising HF which is substantially free from R-245fa (or which contains substantially no R-245fa) is obtained by a distillation operation in which a distillate comprising an azeotropic mixture of R-245fa and HF is obtained, and a portion of the distillate is used as reflux.

To the contrary, when the ratio of R-245fa/HF of the feed is larger than that of the azeotropic mixture which is formed at the operation pressure of the distillation step, a distillation bottom product which is substantially free from HF (or which contains substantially no HF) is obtained by a distillation operation in which the distillate comprising the azeotropic mixture of R-245fa and HF is obtained, and a portion of the distillate is used as reflux.

In the separation/purification process according to the present invention as described above, operation conditions are not particularly limited, but appropriately selected depending on a feed composition, an aimed separation/purification extent, utility conditions (for example, a cooling temperature of the distillate, a heating temperature at the bottom of an distillation apparatus and so on), and apparatus limitations (for example, pressure resistance of the apparatus and so on). For example, the operation pressure may be generally in the range between 1 kg/cm$^2$-G and 30 kg/cm$^2$-G, and preferably 1 kg/cm$^2$-G and 20 kg/cm$^2$-G.

Based on the data of the above azeotropic compositions, it has been further found for the first time that the azeotropic composition of R-245fa and HF considerably greatly changes depending on a pressure of the system. According to the extensive studies of the present inventors, it has been clarified that the azeotropic phenomenon of R-245fa and HF shows a maximum value of the R-245fa/HF ratio of the azeotropic composition at a system pressure of about 7 kg/cm$^2$-G, and in the vicinity of that pressure, the R-245fa/HF ratio of the azeotropic composition depends relatively less on the system pressure.

By using the system pressure dependency of the azeotropic phenomenon, there is provided another process in which R-245fa and/or HF is separated/purified by processing the mixture comprising at least R-245fa and HF.

That is, there is provided a process of treating a feed mixture comprising at least R-245fa and HF, which process comprises the steps of:

subjecting the feed mixture to a first distillation stage, whereby a first distillate is obtained which comprises an azeotropic mixture consisting substantially of R-245fa and HF, and a first bottom product is obtained which comprises R-245fa substantially free from HF when an R-245fa/HF ratio (for example, a molar ratio, a mole percentage of R-245fa based on sum of R-245fa and HF and so on, herein after which may be referred to as merely "ratio") of the feed mixture is larger than the R-245fa/HF ratio of the first distillate, or a first bottom product is obtained which comprises HF substantially free from R-245fa when the R-245fa/HF ratio of the feed mixture is smaller than the R-245fa/HF ratio of the first distillate, and subjecting the first distillate to a second distillation stage which is operated at a pressure which is different from that of the first distillation stage, whereby a second distillate is obtained which comprises an azeotropic mixture consisting substantially of R-245fa and HF, and a second bottom product is obtained which comprises R-245fa substantially free from HF when the R-245fa/HF ratio of the first distillate is larger than the R-245fa/HF ratio of the second distillate, or a second bottom product is obtained which comprises HF substantially free from R-245fa when the R-245fa/HF ratio of the first distillate is smaller than the R-245fa/HF ratio of the second distillate.

By recovering the first and/or the second bottom products, R-245fa and/or HF are separated/purified. Namely, the present invention provides a process to separate/purify R-245fa and/or HF.

This process is formed by so combining in series two of the separation/purification processes as described earlier in which a single separation/purification is carried out that they are carried out at different operation pressures, and the distillate which comprises the azeotropic mixture and which is obtained in the first separation/purification process is used as a feed mixture for the second separation/purification process which is operated at a different operation pressure. It is of course possible to repeat such distillation stages more than twice, and there is no particular limitation in the repeating number. In a practical application, twice is sufficient. Thus, the above combined separation/purification process will be explained below with reference to an example in which two distillation stages are combined.

Figure 1:
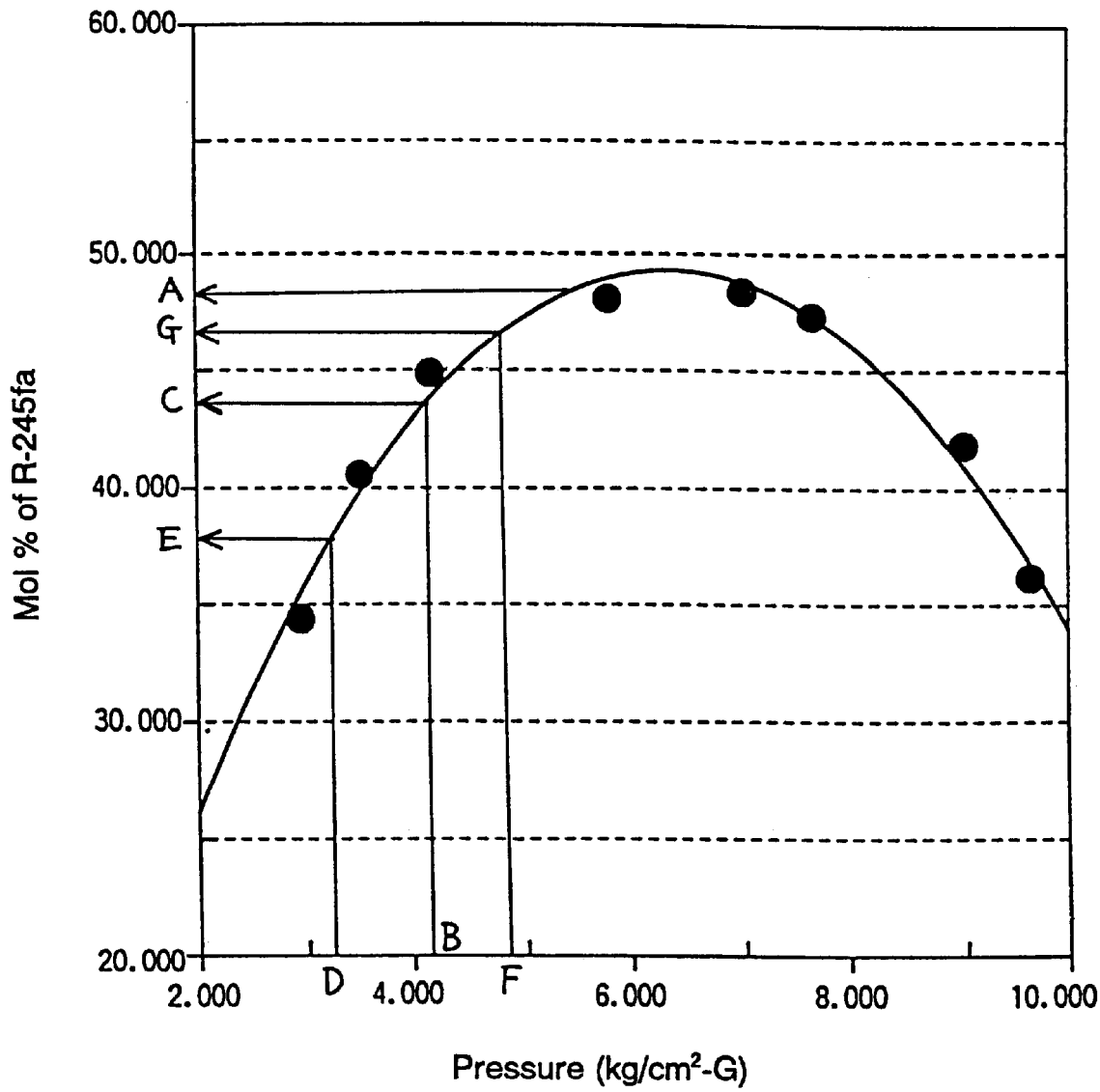
FIG. 1 is a graph which shows an effect of an operation pressure on a composition of an azeotropic mixture according to the present invention.

In the drawing, each numeral indicates as follows:

| 1 | high-pressure distillation column (first distillation stage) | | |
|---|---|---|---|
| 3 | low-pressure distillation column (second distillation stage) | | |
| 5 | feed comprising R-245fa/HF | | |
| 7 | first distillate | 9 | cooler |
| 11 | reflux | 13 | first bottom product |
| 15 | second distillate | 17 | cooler |
| 19 | reflux | 21 | second bottom product |

DETAILED DESCRIPTION OF THE INVENTION

In the first embodiment of the combined separation/purification process as described above, it is characterized in that the R-245fa/HF ratio of the feed mixture is larger than the R-245fa/HF ratio of the first distillate and also larger than the R-245fa/HF ratio of the second distillate, and the R-245fa/HF ratio of the first distillate is larger than the R-245fa/HF ratio of the second distillate.

This embodiment can be easily understood with reference to the graph of FIG. 1 in which the azeotropic data is shown. In the graph of FIG. 1, the axis of ordinate indicates mol % of R-245fa of the azeotropic mixture of R-245fa and HF (i.e. 100×R-245fa/[R-245fa+HF], thus this corresponds to the R-245fa/HF ratio), and the axis of abscissas indicates pressure at which the azeotropic mixture is formed. In the first embodiment, the R-245fa/HF ratio of the feed mixture is indicated by for example A. The first distillation stage is operated at for example a pressure B, and thus the R-245fa/HF ratio of the first distillate is indicated by C. Since A is larger than C (i.e. A>C), the bottom product of the first distillation stage can be made substantially free from HF. Then, the first distillate is subjected to the second distillation stage which is operated at for example a pressure of D so that the R-245fa/HF ratio of the second distillate is E. As clearly seen, C is larger than E (i.e. C>E), and therefore the bottom product of the second distillation stage can be made substantially free from HF.

In the second embodiment of the combined separation/purification process according to the present invention, it is characterized in that the R-245fa/HF ratio of the feed mixture is larger than the R-245fa/HF ratio of the first distillate and also larger than the R-245fa/HF ratio of the second distillate, and the R-245fa/HF ratio of the first distillate is smaller than the R-245fa/HF ratio of the second distillate.

Referring to the graph of FIG. 1, the second embodiment is the same as the above first embodiment except that, in the second embodiment, the second distillation stage is operated at for example a pressure of F, and the R-245fa/HF ratio of the second distillate is then G (thus, G>C), so that the bottom product of the second distillation stage can be substantially free from R-245fa.

In the third embodiment of the combined separation/purification process according to the present invention, it is characterized in that the R-245fa/HF ratio of the feed mixture is smaller than the R-245fa/HF ratio of the first distillate and also smaller than the R-245fa/HF ratio of the second distillate, and the R-245fa/HF ratio of the first distillate is larger than the R-245fa/HF ratio of the second distillate.

Figure 2:
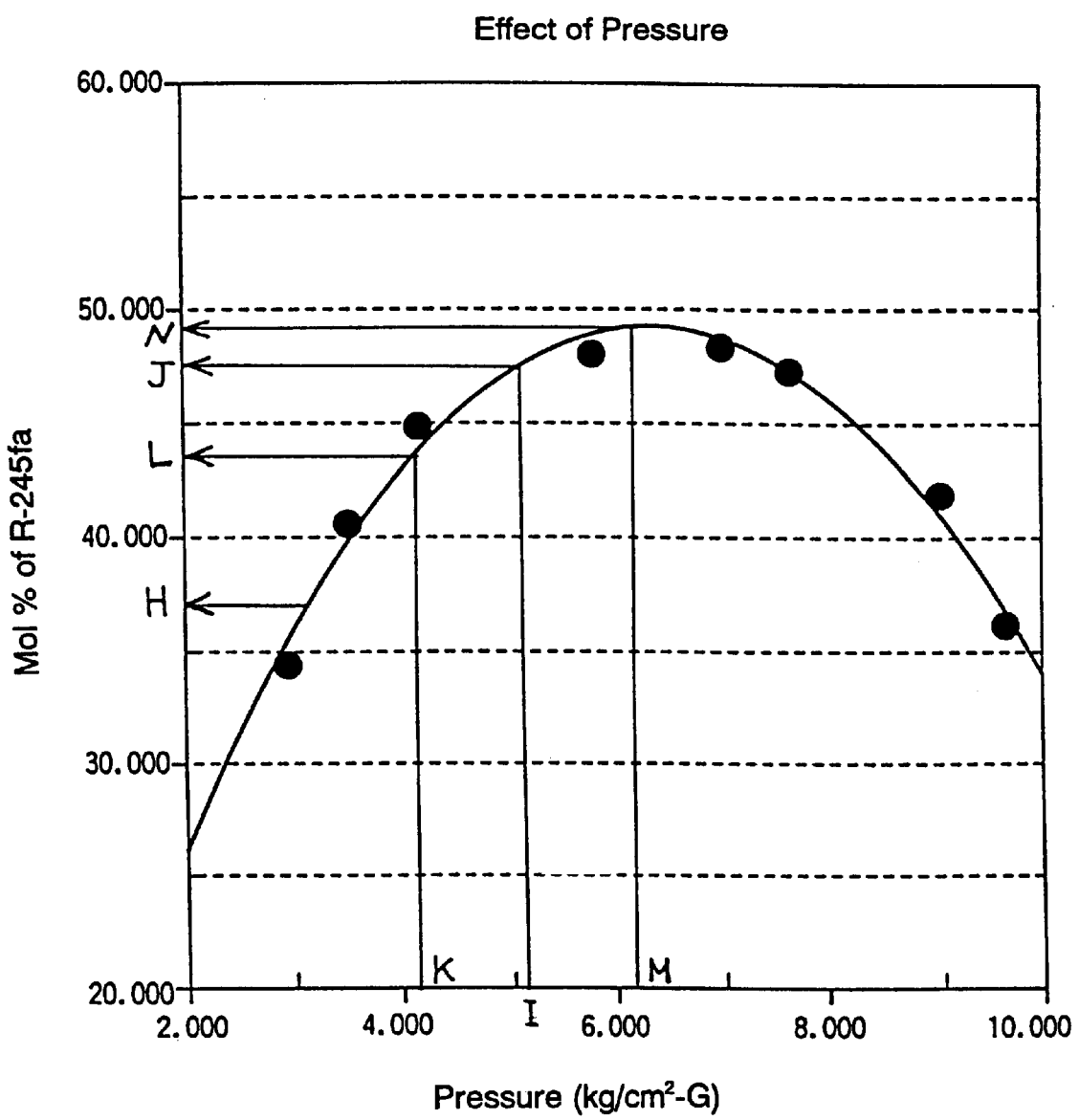
FIG. 2 is a graph which shows an effect of an operation pressure on a composition of an azeotropic mixture according to the present invention.

This embodiment is easily understood with reference to the graph of FIG. 2 which is substantially the same as the graph of FIG. 1. In the third embodiment, the R-245fa/HF ratio of the feed mixture is indicated by for example H. The first distillation stage is operated at for example a pressure of 1, and thus since J>H, the R-245fa/H ratio of the first distillate is indicated by J. Therefore, the first bottom product can be made substantially free from R-245fa. Then, the first As clearly seen, J>L and thus the bottom product of the second distillate can be made substantially free from HF.

In the fourth embodiment of the combined separation/purification process according to the present invention, it is characterized in that the R-245fa/HF ratio of the feed mixture is smaller than the R-245fa/HF ratio of the first distillate and also smaller than the R-245fa/HF ratio of the second distillate, and the R-245fa/HF ratio of the first distillate is smaller than the R-245fa/HF ratio of the second distillate.

Referring to the graph of FIG. 2, the fourth embodiment is the same as the above third embodiment except that, in the fourth embodiment, the second distillation stage is operated at for example a pressure of M, and the R-245fa/HF ratio of the second distillate is then N (thus, N>J), so that the bottom product of the second distillation stage can be substantially free from R-245fa.

In the fifth embodiment of the combined separation/purification process according to the present invention, it is characterized in that the R-245fa/HF ratio of the feed mixture is between the R-245fa/HF ratio of the first distillate and the R-245fa/HF ratio of the second distillate, and the R-245fa/HF ratio of the first distillate is larger than the R-245fa/HF ratio of the second distillate.

Figure 3:
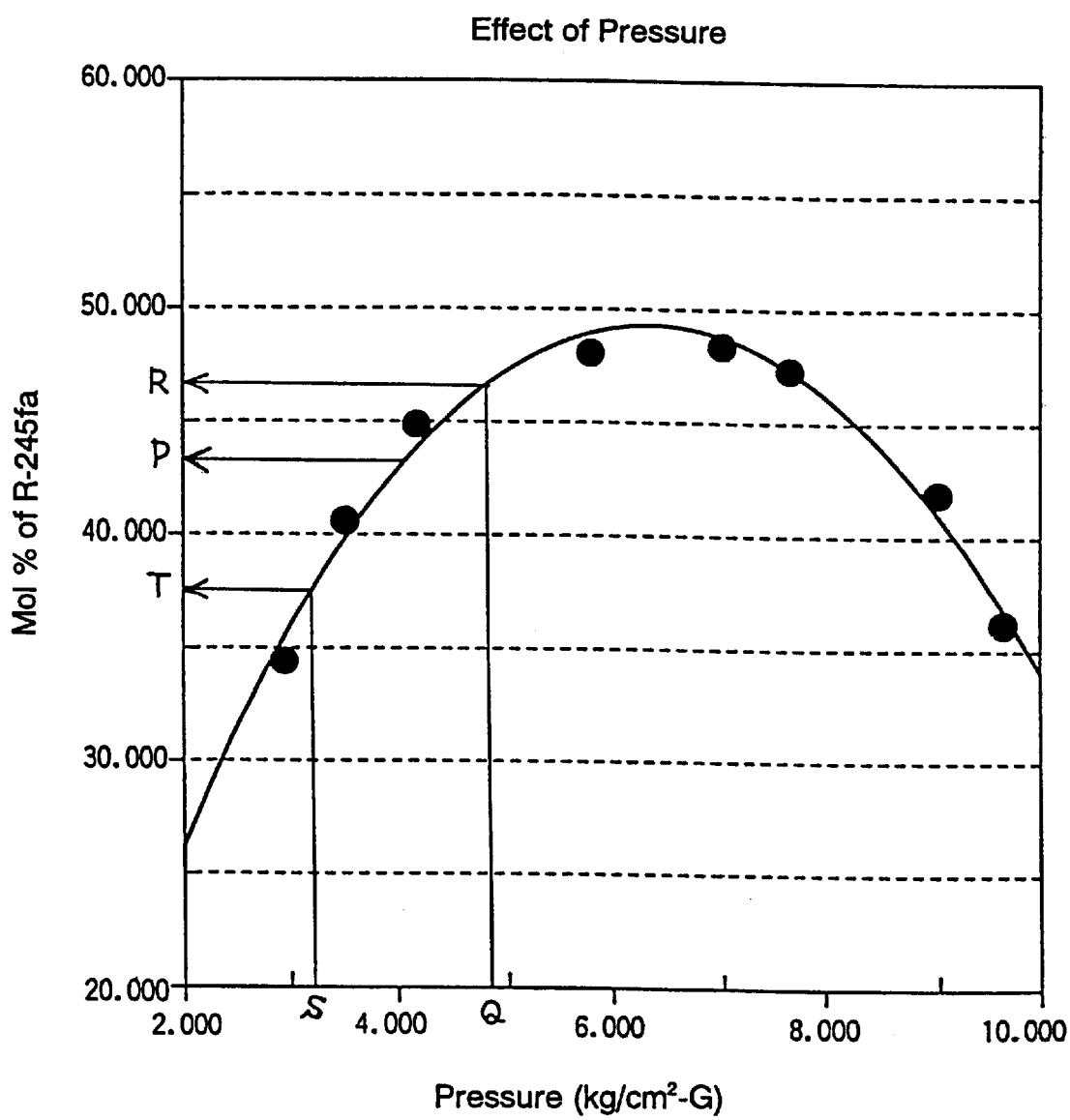
FIG. 3 is a graph which shows an effect of an operation pressure on a composition of an azeotropic mixture according to the present invention.

This embodiment is easily understood with reference to the graph of FIG. 3 which is substantially the same as the graph of FIG. 1. In the fifth embodiment, the R-245fa/HF ratio of the feed mixture is indicated by for example P. The first distillation stage is operated at for example a pressure of Q, and thus the R-245fa/H ratio of the first distillate is indicated by R. Therefore, the first bottom product can be made substantially free from R-245fa. Then, the first distillate is subjected to the second distillation stage which is operated at for example a pressure of S so that the R-245fa/HF ratio of the second distillate is T. As clearly seen, R>T and thus the bottom product of the second distillation stage can be made substantially free from HF.

In the sixth embodiment of the combined separation/purification process according to the present invention, it is characterized in that the R-245fa/HF ratio of the feed mixture is between the R-245fa/HF ratio of the first distillate and the R-245fa/HF ratio of the second distillate, and the R-245fa/HF ratio of the first distillate is smaller than the R-245fa/HF ratio of the second distillate.

Referring to the graph of FIG. 3, in the sixth embodiment, the first distillation stage is operated at for example a pressure of S, and the R-245fa of the first distillate corresponds to T. Since P>T, the bottom product of the first distillation stage can be made substantially free from HF. The second distillation stage is operated at for example a pressure of Q, and then the R-245/HF ratio of the second distillation stage is R (thus, R>T), so that the bottom product of the second distillate can be made substantially free from R-245fa.

Therefore, in the separation/purification process in which the distillation stages are combined according to the present invention, by selecting operation pressures appropriately, R-245fa which otherwise would be distributed to the bottom product is distributed to the distillate as the azeotropic mixture, and/or HF which otherwise would be distributed to the distillate is distributed to the bottom product. To the contrary, HF which otherwise would be distributed to the bottom product is distributed to the distillate as the azeotropic mixture, and/or R-245fa which otherwise would be distributed to the distillate is distributed to the bottom product.

In one preferable case of the first embodiment, when the R-245fa/HF mole ratio of the feed mixture is not less than 1, the first distillation stage is operated at a pressure in the range between about 5 kg/cm$^2$-G and about 8 kg/cm$^2$-G and the second distillation stage is operated at a pressure not more than about 5 kg/cm$^2$-G or not less than about 8 kg/cm$^2$-G.

In this case, since most of R-245fa of which amount is relatively larger in the feed mixture is not distilled off, but obtained as the first bottom product of the first distillation stage, there is provided an advantage in energy consumption. In addition, another advantage is provided in that the smaller the R-245fa/HF ratio in the second distillation stage is, the smaller amount of R-245fa only has to be distilled off in the second distillation stage (thus, a concentration of R-245fa in the second distillate is reduced, and an amount of R-245fa is increased which is obtained as the bottom product).

In one preferable case of the second embodiment, when the R-245fa/HF mole ratio of the feed mixture is not less than 1, the first distillation stage is operated at a pressure not more than about 5 kg/cm$^2$-G or not less than about 8 kg cm$^2$-G, and the second distillation stage is operated at a pressure in the range between about 5 kg/cm$^2$-G and about 8 kg/cm$^2$-G.

In this case, since most of R-245fa of which amount is relatively larger in the feed mixture is not distilled off, but obtained as the first bottom product of the first distillation stage, there is provided an advantage in energy consumption.

In one preferable case of the third embodiment, when the R-245fa/HF mole ratio of the feed mixture is not more than 0.4, the first distillation stage is operated at a pressure in the range between about 5 kg/cm$^2$-G and about 8 kg/cm$^2$-G and the second distillation stage is operated at a pressure not more than about 5 kg/cm$^2$-G or not less than about 8 kg/cm$^2$-G.

In this case, since most of HF of which amount is relatively larger in the feed mixture is not distilled off, but obtained as the first bottom product of the first distillation stage, there is provided an advantage in energy consumption.

In one preferable case of the fourth preferable embodiment, when the R-245fa/HF mole ratio of the feed mixture is not more than 0.4, the first distillation stage is operated at a pressure not more than about 5 kg/cm$^2$-G or not less than about 8 kg/cm$^2$-G, and the second distillation stage is operated at a pressure in the range between about 5 kg/cm$^2$-G and about 8 kg/cm$^2$-G.

In this case, since most of HF of which amount is relatively larger in the feed mixture is not distilled off, but obtained as the first bottom product of the first distillation stage, there is provided an advantage in energy consumption. In addition, other advantages are provided in that the larger the R-245fa/HF ratio of the first distillate is, the smaller amount of HF only has to be distilled off in the first distillation stage (thus, a concentration of HF in the first distillate is reduced, and an amount of HF is increased which is obtained as the first bottom product), and that the smaller the R-245fa/HF ratio of the second distillate in the second distillation stage is, the smaller amount of R-245fa only has to be distilled off in the second distillation stage (thus, a concentration of R-245fa in the second distillate is reduced).

In the above cases, the second distillate may be re-used by mixing with the feed mixture to be supplied to the first distillation stage. Further, HF obtained as the bottom product may be re-circulated to the reaction system which produces R-245fa. R-245fa obtained as the second bottom product (and R-245fa as the first bottom product if available) may be used for other predetermined application as it is or after being subjected to conventional purification treatment. The applications of the products thus obtained in the distillation stages are generally applicable to other cases which will be explained below.

When the feed mixture to be supplied to the first distillation stage contains, in addition to R-245fa and HF, other component, it is merely distributed to the distillate or the bottom product depending on its boiling point or its azeotropic point with HF when it forms an azeotropic mixture with HF.

In one preferable case of the fifth embodiment, when the R-245fa/HF mole ratio of the feed mixture is in the range between about 0.4 and about 1, the first distillation stage is operated at a pressure in the range between about 5 kg/cm$^2$-G and about 8 kg/cm$^2$-G and the second distillation stage is operated at a pressure not more than about 5 kg/cm$^2$-G or not less than about 8 kg/cm$^2$-G.

In one preferable case of the sixth embodiment, when the R-245fa/HF mole ratio of the feed mixture is in the range between about 0.4 and about 1, the first distillation stage is operated at a pressure not more than about 5 kg/cm$^2$-G or not less than about 8 kg/cm$^2$-G, and the second distillation stage is operated at a pressure in the range between about 5 kg/cm$^2$-G and about 8 kg/cm$^2$-G.

The separation/purification process as described above in which the higher pressure distillation stage and the lower pressure distillation stage are combined may be carried out under any operation conditions merely provided that the operation pressures are selected to provide the azeotropic compositions of the distillates which are different from each other. It is of course possible to select more optimal operation conditions under considerations of energy consumption and facility cost.

Considering cooling conditions of the distillate and also heating conditions at the bottom of the distillation column, it is appropriate to select the higher operation pressure and the lower operation pressure in the range between about 1 kg/cm$^2$-G and about 30 kg/cm$^2$-G, and preferably between about 1 kg/cm$^2$-G and about 20 kg/cm$^2$-G.

The distillation stage(s) may be carried out batch-wise or continuously when they are combined or when a single distillation stage is carried out. Generally, the distillation stage(s) is preferably carried out continuously. There is no specific limitation as to the type of the distillation apparatus to be used, and the conventional distillation apparatus (for example, a packed column, a plate column and so on) may be used. Optionally, when the synthesis of R-245fa is carried out in a liquid phase reaction, the distillation apparatus may be integrated with a reactor. In one concrete embodiment, fluorination of pentachloropropane is carried out in HF as a solvent, and R-245fa produced is distilled off from a distillation column which also functions as a reactor.

Best Mode for Carrying Out the Invention

Figure 4:
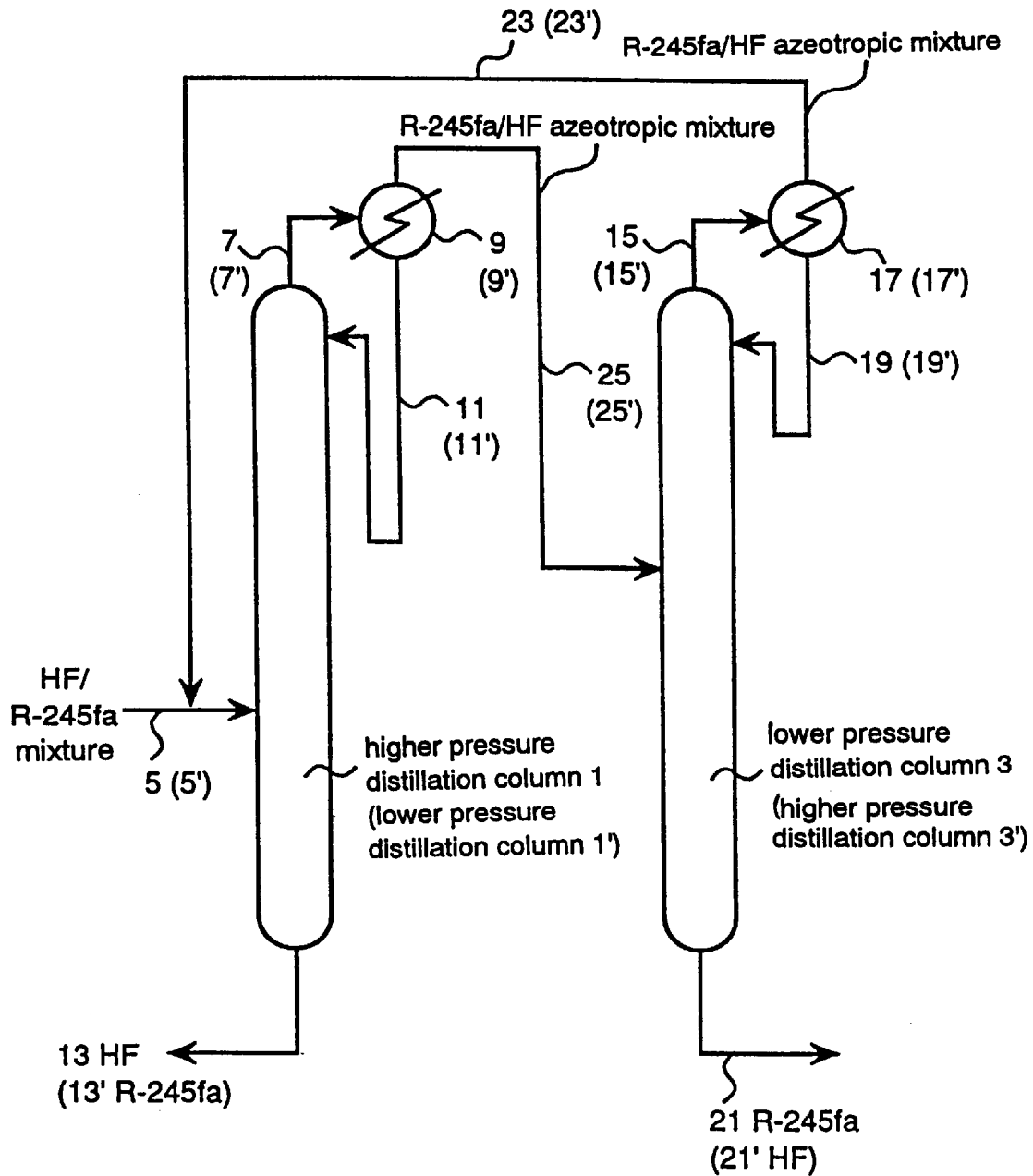
FIG. 4 schematically shows a flow sheet of a preferable embodiment of the present invention in which R-245fa and HF are separated/purified.

In FIG. 4, there is schematically shown a flow sheet of one embodiment of the combined higher pressure and lower pressure distillation operations in which the first distillation stage and the second distillation stage are carried out at a pressure not more than about 8 kg/cm²-G. This process comprises the first distillation stage 1 which is a higher pressure column and the second distillation stage 3 which is a lower pressure column and continuously processes the feed mixture 5 which comprises at least R-245fa and HF. The feed mixture 5 may be for example a reaction effluent from a reaction system which produces R-245fa or may be from any other source provided that it comprises R-245fa and HF.

The feed mixture 5 is first introduced into the higher pressure column 1 (its operation pressure is for example about 7 kg/cm²-G) which is operated so as to distill off the azeotropic mixture of R-245fa and HF, and the first distillate 7 comprising the azeotropic mixture is cooled by the cooler 9 to be condensed. A portion of the condensate is returned to the top of the column as the reflux 11 so as to carry out the first distillation stage. When the R-245fa/HF ratio of the feed mixture to be supplied to the first distillation stage is smaller than the R-245fa/HF ratio of the azeotropic mixture at the operation pressure of the first distillation stage, substantially all of R-245fa is distilled off with HF of which amount is such that it forms the azeotropic mixture with the distilled off R-245fa, so that remaining HF which is substantially free from R-245fa is obtained as the bottom product 13 of the higher pressure distillation column 1.

A remaining fraction 25 balanced with the reflux 11 returned to the distillation column 1 is supplied to the second distillation stage 3 (its operation pressure is for example about 3 kg/cm²-G) as the feed mixture. Also, the second distillation stage is operated so as to distill off the azeotropic mixture of R-245fa and HF as the second distillate 15. As in the first distillation stage, the second distillate 15 is cooled by the cooler 17, and a portion of the cooled distillate is returned to a top of the column as the reflux 19. Since the second distillation stage is at the operation pressure which is lower than that of the first distillation stage, the R-245fa/Hf ratio of the second distillate is smaller than that of the first distillate so that substantially all HF is distilled off with R-245fa of which amount forms the azeotropic mixture with the substantially all HF. Thus R-245fa which is substantially free from HF is obtained from the bottom product 21.

The R-245fa/HF mixture 23 which is balanced with the reflux 19 may be recycled to the feed mixture 5 to be supplied to the first distillation stage 1 as shown. Alternatively, since the mixture contains much less HF relatively to the feed mixture 5, HF is removed from the mixture by the conventional treatment such as alkaline washing or water washing so that R-245fa may be recovered.

In this embodiment, since most of HF of which amount in the feed mixture is relatively large is not distilled off but obtained as the first bottom product 13 of the first distillation stage 1, there is provided an advantage as to the energy consumption. Further advantages are in that when the operation pressure of the first distillation stage is higher, less amount of HF has to be distilled off in the first distillation stage (and thus a concentration of HF of the first distillate 7 is reduced, and also an amount of HF obtained as the first bottom product is increased), and that when the operation pressure of the second distillation stage is lower, a less amount of R-245fa only has to be distilled off in the second distillation stage 3 (and thus a concentration of R-245fa of the second distillate 15 is reduced, and also an amount of R-245fa as the second bottom product 21 is increased).

Since the pressure dependency of the azeotropic phenomenon of the R-245fa and HF shows a maximal point, there are two different operation pressures which provide the same azeotropic composition. Thus, alternatively, it is possible to operate either or both of the distillation stages at the higher operation pressure which distills off the same azeotropic mixture as the lower operation pressure. For example, the first distillation stage is operated at a pressure of about 7 kg/cm²-G and the second distillation stage is operated at a pressure of about 10 kg/cm²-G. Also, the contrary manner to the above embodiments may be used (i.e. it is possible to operate either or both of the first and the second distillation stages at an operation pressure higher than about 8 kg/c²-G). Therefore, any of the following embodiments may be carried out: The both of the distillation stages are carried out at an operation pressure lower than about 8 kg/cm²-G; the both of the distillation stages are carried out at an operation pressure higher than about 8 kg/cm²-G; and one of the distillation stages is carried out at an operation pressure higher than about 8 kg/cm²-G, and the other is carried out at an operation pressure lower than about 8 kg/cm²-G.

The present process which treats a feed mixture having the R-245fa/HF ratio higher than that of the azeotropic mixture formed at the operation pressure of the first distillation stage (which feed mixture is referred to as feed mixture 5') may be carried out using, for example, apparatus which comprises a lower pressure distillation column (its operation pressure is for example 3 kg/cm²-G) as the first distillation stage 1', and a higher pressure distillation column (its operation pressure is for example 7 kg/cm² -G) as the second distillation stage 3'.

The feed mixture 5' is first introduced into the lower pressure distillation column 1', and the first distillation stage is carried out in which an azeotropic mixture 7' is distilled off, and cooled and condensed by a cooler 9' and a portion of the condensate is returned to a top of the column as reflux 11'. Since the R-20 245fa/HF ratio of the feed mixture to be supplied to the fit at distillation stage is larger than that of the azeotropic mixture formed at the operation pressure of the first distillation stage, substantially all HF which is supplied to the first distillation stage is distilled off with R-245fa of which amount corresponds to an amount required to form the azeotropic mixture with the substantially all HF, and the rest of R-245fa is obtained as the bottom product 13' which is substantially free from HF.

The remaining fraction 25' which is obtained by subtracting the reflux 11' from the first distillate 7' is supplied to the second distillation stage 3' as a feed mixture. Also, in the second distillation stage, an azeotropic mixture is distilled off from a top of the column as the second distillate 15'. As in the first distillation stage, the distillate is cooled by the cooler 17' and a portion of the cooled distillate is returned to a top of the column as reflux 19'. Further, the second bottom product 21' comprising HF which is substantially free from R-245fa is obtained from the bottom of the second distillation stage 3'.

In this embodiment, since the fist distillation stage 1' is operated at an operation pressure lower than the second distillation stage 3', a concentration of HF of the azeotropic mixture 7' distilled off from the first distillation stage is larger than a concentration of HF of the azeotropic mixture 15' distilled off from the second distillation stage. Since such R-245fa/HF mixture 25' is supplied to the second higher pressure distillation stage 3', substantially all R-245fa which is supplied to the second distillation stage is distilled off so as to form the azeotropic mixture with HF, whereby the bottom product 19 of the second distillation stage is substantially free from R-245fa.

In this embodiment, since most of R-245fa of which amount is relatively large is not distilled off but obtained as the first bottom product 13' of the first distillation stage 1', there is provided an advantage as to the energy consumption. Further advantages are in that when the operation pressure of the first distillation stage is lower, a less amount of R-245fa only has to be distilled off in the first distillation stage (and thus a concentration of R-245fa of the first distillate 7' is reduced, and also an amount of R-245fa obtained as the first bottom product 13' is increased), and that when the operation pressure of the second distillation stage 3' is higher, a less amount of HF only has to be distilled off in the second distillation stage (and thus a concentration of HF of the second distillate 15' is reduced, and also an amount of HF obtained as the second bottom product 21' is increased).

As in the above explanation, it is also possible to utilize that distillates having the same compositions may be obtained at different operation pressures based on the azeotropic phenomenon of the R-245fa/HF system showing the maximal point in the pressure dependency.

EFFECTS OF THE INVENTION

By the process of separating/purifying R-245fa according to the present invention in which the distillation employing the azeotropic mixture of the present invention is used, R-245fa or HF is effectively separated/purified even without the conventional alkaline washing or water washing, and separated/purified HF may be re-used or used for other application.

Further, when the present invention is carried out with combining two distillation stages operated at different pressures, HF and R-245fa are effectively separated/purified.

EXAMPLES

Example 1
(Measurement of Vapor-liquid Equilibrium of R-245fa and HF)

R-245fa and HF were charged in a bomb at a predetermined ratio, and a liquid phase sample and a vapor phase sample were obtained after the system reached the vapor-liquid equilibrium. As to concentrations of R-245fa and HF, the samples were analyzed.

The analysis results (concentrations of R-245fa in mol % of the liquid phase and the vapor phase) are shown below (the balances are concentrations of HF):

| Temp. (° C.) | Pressure (kg/cm$^2$-G) | Liquid Phase (mol %) | Vapor Phase (mol %) |
|---|---|---|---|
| 50 | 3.50 | 9.5% | 30.5% |
| 50 | 4.05 | 24.2% | 40.1% |
| 50 | 4.20 | 38.7% | 42.8% |
| 50 | 4.15 | 56.1% | 45.0% |
| 50 | 3.55 | 76.5% | 51.3% |
| 50 | 2.60 | 90.0% | 65.0% |

Figure 5:
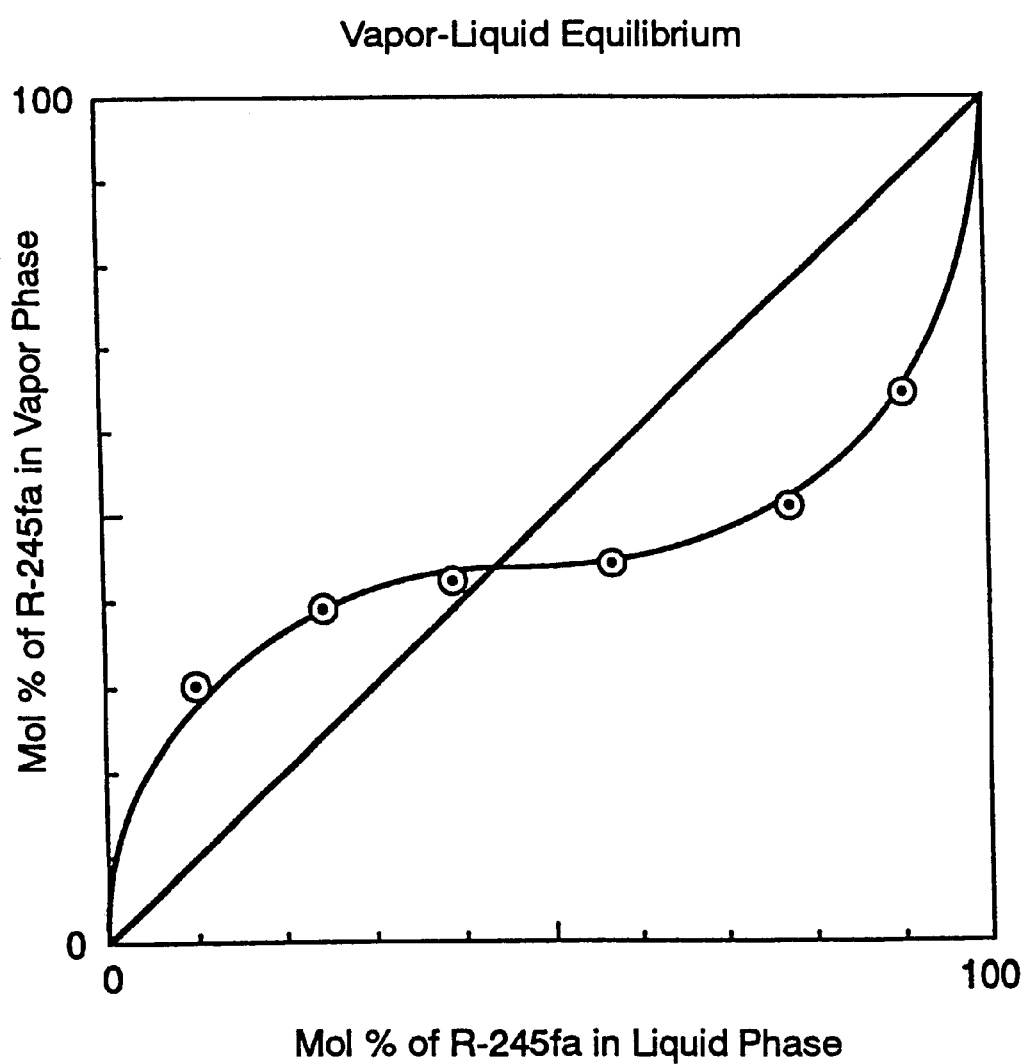
FIG. 5 is a graph which shows results of vapor-liquid equilibrium measurement of an R-245fa/HF system.

The above results are shown in the graph of FIG. 5. As obviously seen from FIG. 5, the R-245fa/HF system has the azeotropic point. In the case as shown, the azeotropic temperature is 50° C., the azeotropic pressure is 4.2 kg/cm$^2$-G, and the azeotropic composition was R-245fa (45 mol %)/HF (55 mol %).

Example 2
(Relationship Between Pressure and Azeotropic Composition)

The pressure of the R-245fa/HF system was variously changed by changing the temperature of the system similarly to Example 1, and the azeotropic temperature and the azeotropic composition (mol % of R-245fa) at each pressure were measured. The results are shown in Table below and also in FIGS. 1 to 3:

| Pressure (kg/cm$^2$-G) | Azeotropic Temp. (° C.) | Liquid & Vapor Phases (mol %) |
|---|---|---|
| 2.95 | 40 | 34.5% |
| 3.50 | 45 | 40.8% |
| 4.20 | 50 | 45.0% |
| 5.80 | 60 | 48.2% |
| 7.00 | 67 | 48.5% |
| 7.65 | 70 | 47.4% |
| 9.00 | 77 | 42.1% |
| 9.60 | 80 | 36.3% |

It is seen from the above results, the azeotropic composition of the R-245fa/HF system greatly depends on the system pressure.

What is claimed is:

1. The azeotropic mixture consisting essentially of 1,1,1,3,3-pentafluoropropane and hydrogen fluoride, wherein under a pressure in a range 2.0 kg/cm$^2$-gauge to 10 kg/cm$^2$-gauge, the mixture has a 1,1,1,3,3-pentafluoropropane/hydrogen fluoride molar ratio in a range of above 25 to below 50 molar α of R-245fa and the remainder HF.

2. The azeotropic mixture according to claim 1, wherein under a pressure in a range of 4.2 kg/cm$^2$-gauge, the mixture has a 1,1,1,3,3-pentafluoropropane/hydrogen fluoride molar ratio of 45/55 and a boiling point of 50° C.

3. The azeotropic mixture of claim 1, wherein the boiling point is about 40 to about 80 ° C.

4. An azeotropic mixture consisting essentially of 1,1,1,3,3-pentafluoropropane and hydrogen fluoride, wherein said azeotropic mixture is formed under pressure in a range of about 2.95 kg/cm$^2$-gauge to about 9.60 kg/cm$^2$-gauge at a temperature in a range of about 40 to about 80 ° C., the resulting azeotropic mixture has a 1,1,1,3,3-pentafluoropropane/hydrogen fluoride molar ratio in a range of about 34.5/65.5 to about 48.5/51.5.

* * * * *